United States Patent
Harner

Patent Number: 6,118,520
Date of Patent: *Sep. 12, 2000

[54] DUAL ANALYSIS PROBE

[75] Inventor: Richard S. Harner, Midland, Mich.

[73] Assignee: The Dow Chemical Company, Midland, Mich.

[*] Notice: This patent issued on a continued prosecution application filed under 37 CFR 1.53(d), and is subject to the twenty year patent term provisions of 35 U.S.C. 154(a)(2).

[21] Appl. No.: 08/768,422

[22] Filed: Dec. 18, 1996

[51] Int. Cl.$^7$ .................................................. G01N 21/00
[52] U.S. Cl. .......................... 356/73; 356/436; 356/136; 356/346
[58] Field of Search .............................. 356/73, 436, 136, 356/346

[56] References Cited

U.S. PATENT DOCUMENTS

| | | | |
|---|---|---|---|
| 3,752,584 | 8/1973 | Schildkraut | 356/74 |
| 3,946,224 | 3/1976 | Allera et al. | 356/28 |
| 4,643,573 | 2/1987 | McLachlan et al. | 356/338 |
| 4,672,218 | 6/1987 | Chrisman et al. | 250/574 |
| 4,678,326 | 7/1987 | Harjunmaa | 356/73 |
| 4,707,134 | 11/1987 | McLachlan et al. | 356/342 |
| 4,753,530 | 6/1988 | Knight et al. | 356/73 |
| 4,768,879 | 9/1988 | McLachlan et al. | 356/301 |
| 4,826,313 | 5/1989 | Schar et al. | 356/51 |
| 4,829,186 | 5/1989 | McLachlan et al. | 250/373 |
| 4,835,389 | 5/1989 | Doyle | 250/343 |
| 4,909,588 | 3/1990 | Hamer et al. | 350/96.2 |
| 5,051,551 | 9/1991 | Doyle | 250/341 |
| 5,241,368 | 8/1993 | Ponstingl et al. | 356/73 |
| 5,365,326 | 11/1994 | Chrisman et al. | 356/28.5 |

OTHER PUBLICATIONS

Harrick, N. J. Internal Reflection Spectroscopy, (1967) Lib. Congress Cat. No. 67–13944, pp. 88,89,94,95,124,125.

*Primary Examiner*—Frank G. Font
*Assistant Examiner*—Reginald A. Ratliff

[57] ABSTRACT

A single fiber optic probe capable of measuring at least two different properties of a medium. More specifically, a single probe having an integral optical element which is capable of directing light to perform at least two distinct spectrometric analyses on a medium. For example, the single probe may be used to monitor a solid phase and dissolved solids in a multiphase medium.

18 Claims, 3 Drawing Sheets

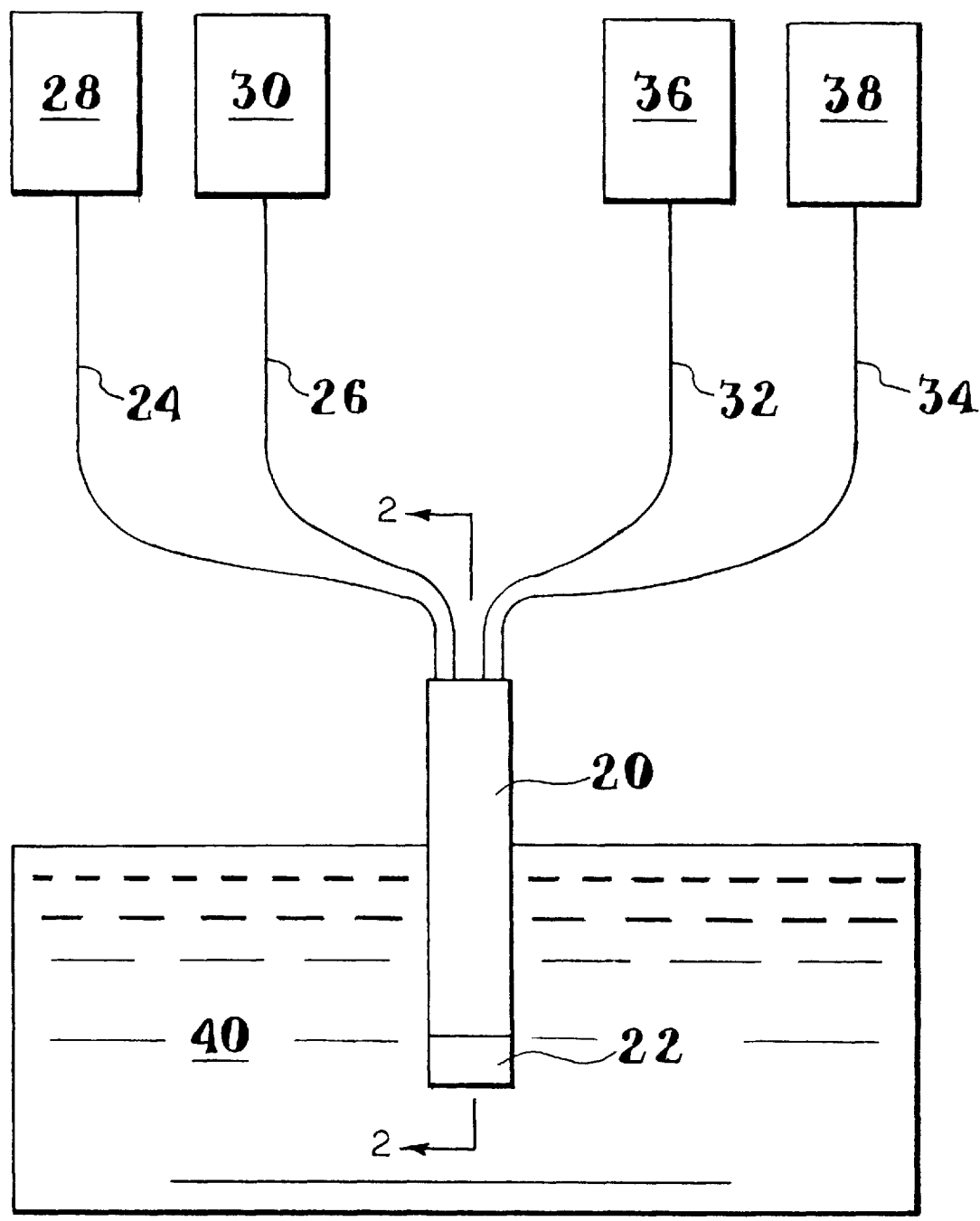

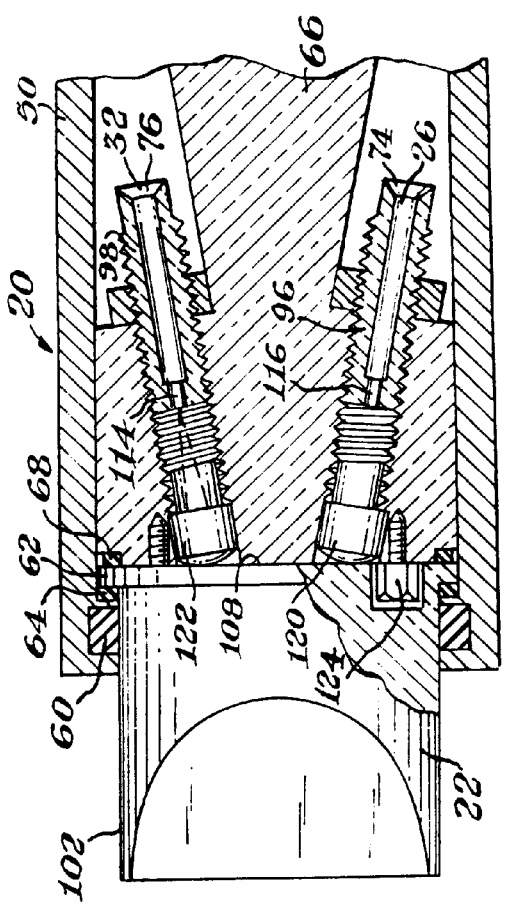
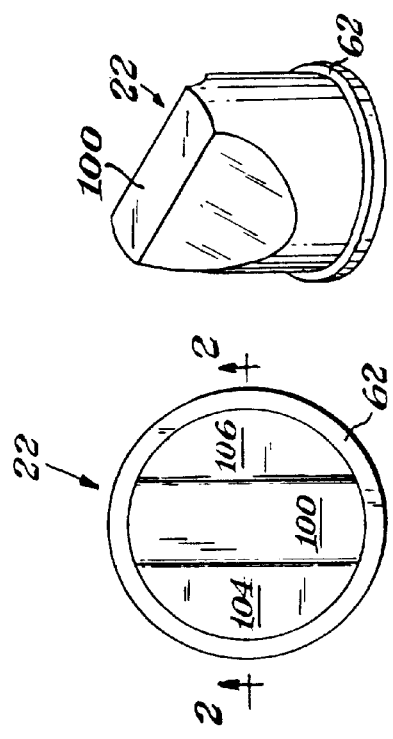
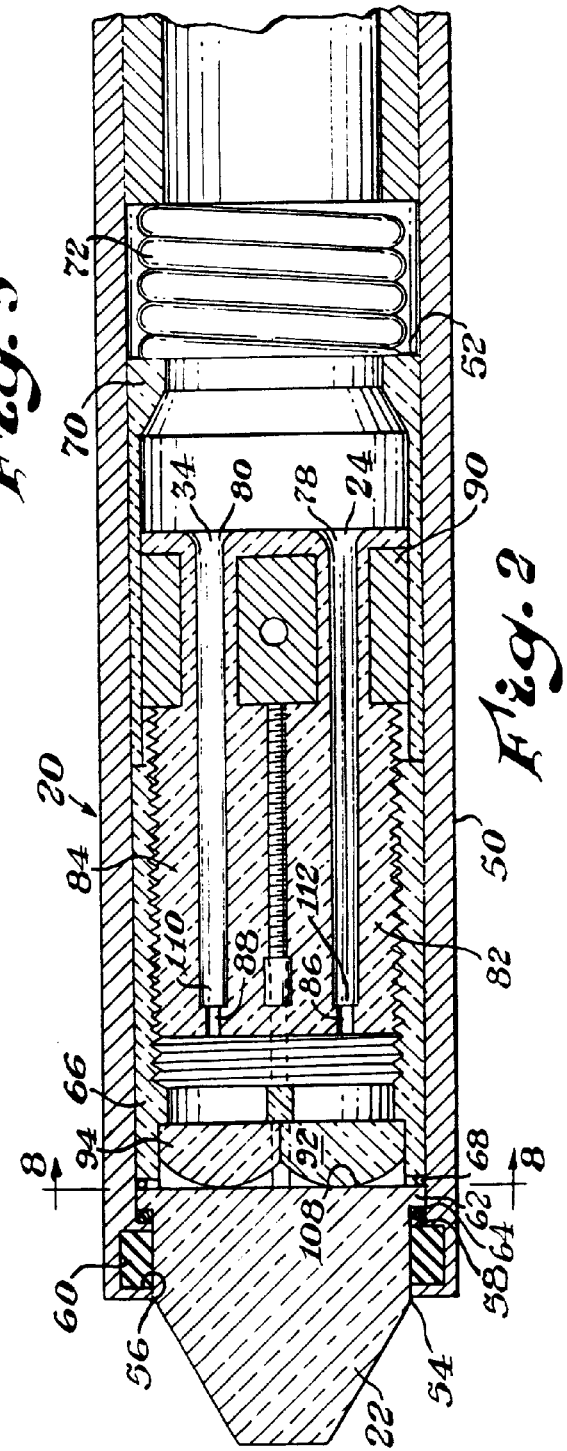

DUAL ANALYSIS PROBE

FIELD OF THE INVENTION

This invention relates to spectrometric analytical methods and an apparatus which includes a fiber optic probe capable of measuring at least two different properties of a medium.

BACKGROUND

Crystalline products can be manufactured by a number of known processes in which crystals are formed in a supersaturated fluid medium or mother liquor. Crystal purity depends in part on the rate of crystal growth. In order for crystallization processes to progress most efficiently, the processes typically depend on determining the onset of crystallization. Probes capable of backscatter analysis can be used to detect particles and thus to determine the onset of crystallization (see, for example, U.S. Pat. No. 4,672,218 to Chrisman); however, once crystallization begins, adjusting the system to adequately reduce the rate of crystallization can be difficult. Thus, a probe capable of better anticipating crystallization would achieve better process control in crystallization processes.

SUMMARY OF THE INVENTION

The present invention includes an improved probe for spectrometric analysis which uses light or spectral radiation transmitted through the probe such that the light interacts with a fluid medium, wherein the improvement comprises an essentially monolithic optical element which is suitable for contact with the fluid medium and which is capable of directing transmitted light to interact with the fluid medium to perform at least two distinct spectrometric analyses. Thus, monitoring of both the solid and solution phase of a medium may be done simultaneously with at least one embodiment of the probe of the present invention. The types of spectrometric analyses that may be performed with the present probe include, for example, attenuated total reflectance (ATR), light scatter analysis, image analysis, and refractive index (RI) determination. Light scatter analysis may include backscatter analysis, Raman, Rayleigh scattering, and fluorescence, for example.

One embodiment of the probe generally comprises a probe body having an internal cavity which is in spectrometric communication with the space exterior to the probe through an optical element. The optical element is capable of directing light in at least two distinct patterns. The probe has a controlled means for transmitting light to the optical element so that the light interacts with the fluid medium. A receiving means is used to receive the light after the light interacts with the fluid medium.

A preferred embodiment of the present invention is a single probe capable of ATR analysis and particle detection. The probe is preferably capable of direct insertion into an industrial process. U.S. Pat. No. 4,829,186 to McLachlan, which is herein fully incorporated by reference, describes the critical limits of ATR analysis. The particle detection system is preferably designed such that light from a separate pair of fibers traverses the optical element on a path different from an ATR path of light, for example, orthogonal to the ATR path of light. A beam of light from the particle detection system exits a surface of the optical element, interacts with particles in the medium, and is scattered back and collected by an optical fiber. The probe of this invention allows simultaneous or sequential determination of ultraviolet (UV) absorbing analytes dissolved in the liquid phase and particle detection of these same analytes in the solid phase in a slurry. Nucleation can be detected while the concentration of an analyte remaining in solution is monitored. For a description of nucleation detection using backscatter analysis, see, for example, U.S. Pat. No. 4,672,218 to Chrisman which is herein fully incorporated by reference.

The probe of the present invention may be used, for example, in a concentrated two phase system. The probe may be useful in any of the known applications where ATR, and/or particle detection analysis can be beneficially employed in process or laboratory environments. The probe may be used as a monitoring element in a control scheme for controlling supersaturation, particularly if an estimate of the saturation zone over a range of temperatures is known before the probe is employed. Therefore, supersaturation may be controlled by effecting the cooling rate in cooling crystallization based upon measurements of supersaturation obtained from one probe embodiment.

BRIEF DESCRIPTION OF THE DRAWINGS

FIG. 1 is a schematic diagram of an analytical system including the probe of the present invention.

FIG. 2 is a partial cross-sectional view of the probe taken along reference line 2—2 of FIG. 1.

FIG. 3 is a view like FIG. 2 only taken along a reference line which is orthogonal to reference line 2—2 of FIG. 1.

FIG. 4 is an isometric view of one embodiment of the integral window or optical element used in the probe of FIGS. 1–3.

FIG. 5 is a top view of the optical element depicted in FIG. 4.

DETAILED DESCRIPTION OF THE INVENTION

Figure 6:
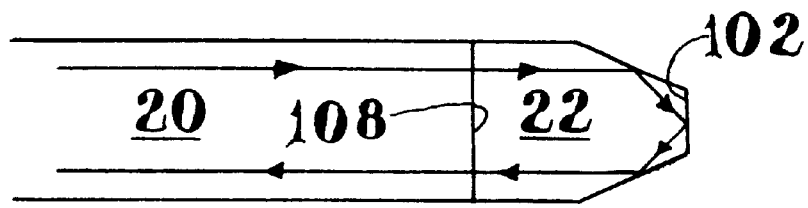
FIGS. 6 and 7 and show a schematic view of the probe and optical element and the pattern that light may travel through the optical element to perform ATR, and backscatter analysis respectively.

Referring to FIG. 1, therein is shown a system utilizing probe 20 of the present invention. Optical element 22 of probe 20 is inserted into fluid medium 40 for analysis of the medium 40. Probe 20 is connected by means for transmitting light 24, 26 to light sources 28, 30, respectively. Probe 20 is also connected by receiving means 32, 34 to detectors 36, 38, respectively which detect light transmitted through the receiving means. Means for transmitting light and receiving means for receiving light both comprise elements through which light can travel. More specifically, means for transmitting light refer to at least one element capable of transmitting light to an optical element. Similarly, receiving means refers to at least one element capable of receiving light exiting from an optical element.

Means for transmitting light and a receiving means for receiving light can include an optical fiber as shown in the figures, a bundle of fibers, etc. A single output fiber could be used as the receiving means for both ATR and nucleation detection if positioned properly, for example, along the axis of the probe. Alternatively, a bundle of fibers could be used in order to collect more light. For nucleation detection, a single fiber could be used to both send and receive the light. A single fiber could also be used to send light in two directions, for example, by using a beam splitter or a dichroic filter.

Suitable light sources and detector means depend on the wavelength of light to be employed and the technique used to analyze the fluid medium. For example, to perform ATR analysis, ultraviolet light may be transmitted from a deuterium lamp and detected by a diode array or a spectrograph. Backscatter analysis may be performed by transmitting light from a light emitting diode or a laser diode and detecting the light with a silicon photodiode or a photomultiplier respectively. Refractive index determination may be performed, for example, using near infrared (NIR) light from a light emitting diode and detected with silicon photodiodes or a photodiode array.

Referring now to FIG. 2, therein is shown probe 20 which comprises a generally hollow cylindrical probe body 50 defining a cylindrical interior cavity 52. The probe body 50 includes end portion 54 which defines a cylindrical opening. A peripherally continuous groove 56 is defined in the end portion 54 adjacent the opening, and a peripherally continuous lip 58 is located immediately inwardly of groove 56. An optical element or integral window 22 is located in the opening of end portion 54 and is sealed peripherally to probe body 50 by o-ring 60 seated in groove 56. The optical element 22 includes a peripherally continuous lip 62 which is continuous about its lower base and which is juxtaposed with lip 58 of the probe body 50. A gasket 64 is seated between lip 58 of probe body 50 and lip 62 of optical element 22. The assembly of optical element 22 and probe body 50 is retained under compression by a brass front insert 66 which is slideably positioned within cavity 52 and which applies pressure peripherally to lip 62 of optical element 22 through a gasket 68 which is seated against optical element 22 and against one end of front insert 66. Insert hood 70 encompasses the opposite end of front insert 66 within cavity 52. Insert hood 70 is engaged with compression spring 72 to transfer pressure resiliently to optical element 22 through front insert 66 and gaskets 64, 68 thereby compressing lip 62 of optical element 22 against lip 58 of probe body 50 to form a liquid tight seal.

Front insert 66 defines threads in which is threadably secured rear inserts 82, 84. Each rear insert 82, 84 defines an elongated channel 78, 80, respectively; the elongated channels 78, 80 are parallel with and on opposite sides of the longitudinal axis of probe 20. The front and rear inserts are held in place by insert thread locks 90. Optical fibers 24, 34 are positioned in channels 78, 80 respectively and communicate optically with optical element 22 through means for focusing light 92, 94 which are optically aligned with channels 78, 80.

Figure 8:
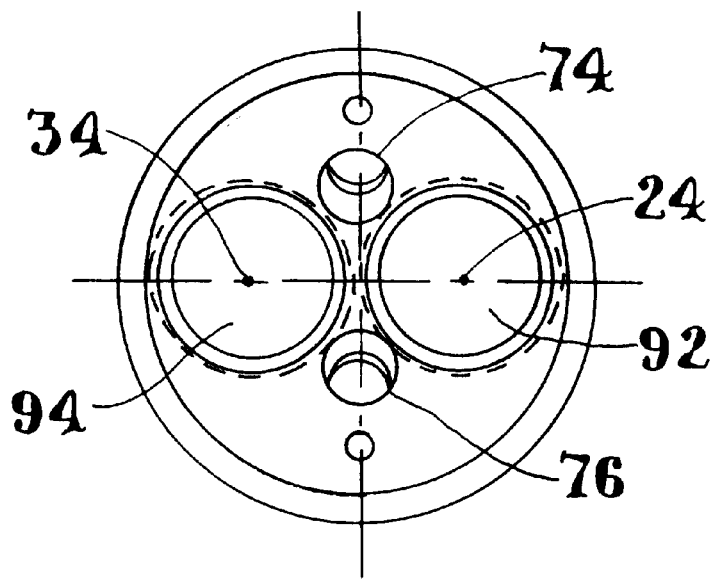
FIG. 8 shows a top view of the probe insert along reference line 8—8 in FIG. 2.

FIG. 3 shows probe 20 along a cross sectional view taken ninety degrees with respect to the plane of the cross sectional view of FIG. 2. FIG. 3 illustrates optical fibers 26, 32 which are arranged orthogonally with respect to fibers 24 and 34 within probe body 50. More specifically, FIG. 3 illustrates rear inserts 96, 98 which define elongated channels 74, 76 (FIGS. 3 & 8) on opposite sides of the longitudinal axis of probe 20 in which optical fibers 26, 32 are positioned. Rear inserts 96, 98 are positioned within probe body 50 in a manner similar to rear inserts 82, 84 as described above. In FIG. 3, optical element 22 is shown in partial cross section, revealing a dual diameter pin 124 which is used to align optical element 22 relative to the optical fibers in order to maintain a precise optical path through the optical element which increases throughput.

Means for focusing light 92, 94 (FIGS. 2 & 8) may be positioned between optical element 22 and the end of each absorbance optical fiber 24, 34 (FIG. 2); and means for focusing light 120, 122 may also be positioned between the optical element 22 and the end of each reflectance optical fiber 26, 32 (FIG. 3).

The term "reflectance optical fiber" refers to an optical fiber capable of sending or receiving light in a manner that permits the light to interact with the medium such that some of the light is reflected by particles which may be present in the medium. Similarly, "absorbance optical fiber" refers to an optical fiber capable of sending or receiving light that interacts with the medium in such a manner that some of the light is absorbed by analytes which may be dissolved in the medium. Examples of means for focusing light include the following: lenses; a prism with focusing surfaces ground on the external surface of the prism; input optical fibers having a relatively small diameter, for example on the order of a few microns; and a bundle of such fine fibers. The means for focusing light 92, 94 are preferably lenses which preferably comprise sapphire, silica or glass, depending on the wavelength of light to be used.

Focused light is desirable because more light impinges upon the optical element at an angle usable for analysis. In ATR, collimated light is useful to define and maximize both the total throughput of the optical element and the actual facet surface area sampled.

In particle detection, lenses define the light intersection zone and can be used to collimate, converge and diverge the emitted and collected light.

FIGS. 4 and 5 show a preferred structure for optical element 22. The optical element 22 is preferably primarily cylindrical. Preferably, the exterior surface 102 of optical element 22 has a flat top 100 and two flat, symmetrical angled cuts 104, 106. Each cut should be at the same angle with respect to normal to the top 100 of optical element 22. To further clarify the structure of the preferred optical element 22 embodiment, FIG. 2 shows a cross-sectional view of the preferred optical element 22 along view 2—2 of FIG. 5; and FIG. 3 shows an elevational side view of the optical element 22 perpendicular to view 2—2 of FIG. 5.

The optical element 22 should be capable of transmitting light of a wavelength or wavelengths at which analysis is to be done. The optical element may be a single prism or a window. The optical element may be shaped, for example, as a truncated cone or, preferably, a truncated chisel as depicted in FIGS. 4 and 5. One advantage of this optical element, generally, is the reduced likelihood of catching solids on the optical element. An optical element in the form of a truncated chisel (as shown in FIG. 4) may provide greater control of the angles of incidence and reflection of the light than an optical element in the form of a truncated cone.

Referring to FIGS. 2, 3 and 5, the internal surface 108 of the optical element 22 refers to the surface facing the cavity 52 of the probe body 50 where the optical fibers are located. The external surface 102 of the optical element 22 refers to the surface facing the space exterior to the probe body 50. When performing ATR, the choice of materials for the optical element 22 is limited by the requirement that the refractive index (n) of the optical element 22 exceeds that of the bulk medium 40. Preferably, the optical element 22 comprises sapphire, but other materials including diamond, spinel, silica, and cubic zirconia may be used depending on the wavelength range of interest. For use in the ultraviolet region (200 to 400 nanometer wavelengths), silica (n=1.51 at 250 nanometers), sapphire (n=1.84 at 250 nanometers) and diamond (n=2.7 at 250 nanometers) have preferred refractive indices and transmissions. Silica is generally useful for samples of relatively low refractive index, such as aqueous solutions. Diamond is relatively expensive and does not transmit efficiently below wavelengths of about 225 nanometers. Thus, sapphire is a preferred material for ATR measurements in the UV wavelength range.

Other wavelength ranges of interest depend on the type of spectrometric analysis performed. For example, absorption spectral analysis may be practiced over a wide spectral range with many different sources and detectors. Backscatter analysis may be practiced at a single wavelength because the wavelength is not as important as whether or not the light is reflected and detectable.

Turning now to preferred spectrometric analyses, the optical element is preferably capable of directing light to perform both attenuated total reflectance and backscatter analysis. Preferred analyses include concentration determination via attenuated total reflectance (ATR), and nucleation detection via backscatter analysis. Alternatively, modifications can be made to the optical element to perform different types of analyses. The optical element is preferably capable of directing the light to perform other measurements including, but not limited to refractive index (RI) determination. The optical element serves as an integral window, and may be composed of several optical elements such that the integral combination is designed to achieve a plurality of measurements as described above. The optical element may have a flat external surface is shown, but a curved surface could be used and may be beneficial as a means to focus light. Also, a coating having a different refractive index than the optical element or a metal coating may be beneficial, for example, in ATR analysis to control the depth of penetration of the evanescent wave. A metal coating may also be employed to reflect the light to prevent its interaction with the medium, for example, to avoid ATR.

The geometry of the probe and optical element must be adapted to the types of analyses to be performed. Different inserts may be used interchangeably in the same probe body by adapting the geometry of the insert in relation to an appropriate optical element to permit the desired measurements. For example, if ATR analysis is desired, any geometry known for ATR may be used. Examples of configurations for ATR optical elements are shown in N. J. Harrick, *Internal Reflection Spectroscopy* (1967), Lib. of Congress Cat. No. 67-13944 which is herein incorporated by reference. Generally, the ATR geometry of the present invention will permit spectral radiation to go through a series of internal reflections so the radiation is directed back into an optical fiber.

In a preferred embodiment shown in the figures, the probe and prism geometry are compatible with backscatter analysis. The geometry to perform backscatter analysis must permit light to exit and reenter the optical element. One way to accomplish this geometry is to position the fibers on perpendicular planes with respect to each other and with respect to the radial axis of the probe as shown in the figures.

In the probe design shown in the figures, the light paths are virtually independent of each other. This does not preclude a design where beam paths arbitrarily cross. Nor does this preclude the possibility of a gap in the optical element on the order of the wavelength of light used to have a Fabry-Perot interferometer in which light from a single source may create interference patterns.

For valid measurements, leaking between the optical element and the ends of the optical fibers should be prevented. Thus, the ends of the optical fibers should be isolated from the fluid medium, for example, by sealing optical element 22 to the probe body 50. The pressures and temperatures in a crystallizer vary greatly so the seals on the probe should withstand such variation if the probe is to be used in a crystallizer. Depending on the operating conditions, suitable sealing means may include, for example, sealing means as described in U.S. Pat. No. 4,909,588 to Harner or sealing means depicted in FIG. 2. The sealing means in FIG. 2 includes a radial O-ring 60 which serves as the primary process seal, and two gaskets 64, 68 serving as secondary seals. In addition, the probe may have a compressive spring 72 positioned within the body 50 for providing a compressive force on the secondary sealing means between the optical element 22, body 50, and the front insert 66. The probe may also have elastomers situated between optical element 22 and insert 66 such that no direct contact is made between the optical element 22 and the insert 66. Sealing may also be done by brazing, if corrosion resistance of the braze material and differential thermal expansion is considered. Other sealing means may be employed based on the application of the probe.

Materials used for various parts of the probe may be any material known in the art to be suitable for probes which are to be inserted into a fluid medium or slurry. For instance, the probe body may be made of stainless steel, a HASTEL-LOY™ alloy, tantalum, etc. depending on the process in which the probe is to be used. Preferably, standardized internal parts are employed to facilitate replacement or substitution of internal parts within the probe body.

Referring now specifically to the manner of operation of probe 20, optical element 22 provides optical communication between the cavity 52 of probe body 50 and the space exterior to probe 20. Within probe body 50 is an input absorbance optical fiber 34 having an end 88 which is optically coupled with an end 86 of an output absorbance optical fiber 24 through optical element 22. Generally, optically coupled means permitting light to be communicated from one to the other. More specifically, the end 88 of the input absorbance optical fiber 34 is brought into close proximity with the optical element 22 and at such angle with respect to the external surface 102 of the optical element 22 as to permit ATR within the optical element 22. The end 86 of output absorbance optical fiber 24 is brought into close proximity with optical element 22 in a position capable of receiving light emitted from the end 88 of fiber 34 after the light performs ATR within optical element 22.

FIG. 3 shows the portion of probe 20 capable of backscatter analysis. Backscatter analysis is done by emitting light into a medium such that the light is reflected back should a solid particle or an interface having a different refractive index than the medium be in a detectable portion of the light path within the medium. One way to achieve backscatter analysis is the use of optical fibers 32 and 26 arranged within probe body 50 so the ends 114 and 116 of the optical fibers 32 and 26 are angled toward each other and are positioned in close proximity with optical element 22. Thus, the ends 114 and 116 of optical fibers 32 and 26 are optically coupled to each other through optical element 22 and through reflection from solids exterior to the probe 20 beyond optical element 22.

The manner of operation of the probe is perhaps easiest to understand by a description of the manner in which the optical element 22 may beneficially direct light in two patterns. Referring to FIGS. 2 and 6, input absorbance optical fiber 34 is optically coupled with the internal surface 108 of the optical element 22 such that light emerging from one end 88 of the input absorbance optical fiber 34 enters optical element 22 through the internal surface 108 of optical element 22 and then is totally internally reflected in optical element 22. The totally internally reflected light then exits the internal surface 108 of optical element 22. An output absorbance optical fiber 24 is positioned within probe 20 so that end 86 of output absorbance optical fiber 24 is optically coupled with the internal surface 108 of optical element 22 and such that totally internally reflected light emerging from the internal surface 108 of optical element 22 enters the one end 86 of the output absorbance optical fiber 24. This generally describes the manner of operation with respect to ATR analysis.

Figure 7:
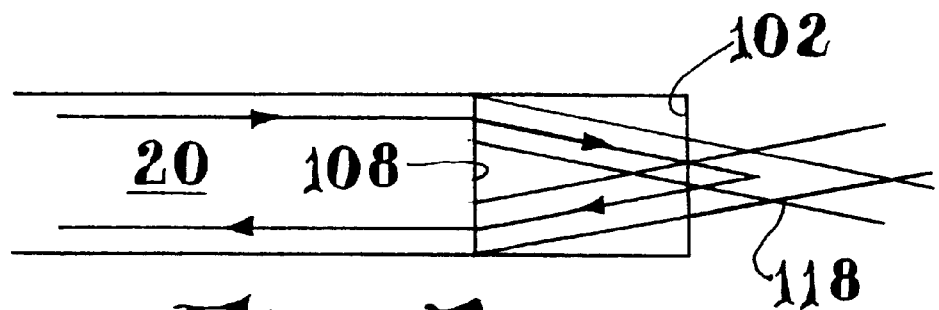

Turning now to FIGS. 3 and 7, the manner of operation with respect to backscatter analysis will be described. An input reflectance optical fiber 32 is positioned within probe 20 so that light emerging from end 114 of the input reflectance optical fiber 32 enters the optical element 22 through the internal surface 108 of optical element 22 and then exits the optical element 22 through the external surface 102 of the optical element 22 to produce an illuminated zone 118. Thus, if a particle or an interface having a different RI than the medium is in the illuminated zone 118, then backscattered light reflected from the particle or interface can enter the external surface 102 of the optical element 22 and then exit the internal surface 108 of the optical element 22. The backscattered light may then enter the end 116 of output reflectance optical fiber 26. Thus, optical fibers 24 and 34 (FIG. 2), and 26 and 32 (FIG. 3) provide means for transmitting light reversibly through the probe such that the light is capable of interacting with a fluid medium 40 put in contact with the optical element 22.

The ability to combine a probe capable of ATR with a probe capable of particle detection is unexpected, particularly using the same optical element, because ATR is typically done with a relatively thick optical element and nucleation detection is typically done with a thin window so more light enters the solution and can be reflected from solid particles in the solution. However, the probe of the present invention is capable of such dual measurements. Another secondary technique to couple with ATR is image analysis which may be useful, for example, to determine the size of a particle. With image analysis, particles can be digitally counted and sized. Well known image analysis techniques include image transfer optics; coherent fiber optic bundles; and direct image capture. Imaging may be performed using an optical element which is polished on both sides or otherwise polished in a known manner.

ATR alone may be used for qualitative as well as quantitative evaluations. Thus, materials present may be identified from the resulting absorption spectrum. Quantitation is possible with ATR but may be limited, for example, by path length inconsistency, and poor surface contact for solids. Other uses for ATR include image analysis of objects in contact with the crystal, determination of optical constants, and surface phenomenon including adsorption, desorption in thin films, conductivity of fiber, etc. Preferably, in the probe of the present invention, ATR is used for concentration determination.

In general, in situ ATR measurements can be made by the use of a probe having a probe body formed of material that can be immersed in a fluid medium wherein the fluid medium contains a constituent capable of absorbing light of a specific wavelength. Preferably, light of substantially constant intensity is emitted from a source remote from the medium via one or more optical fibers to an optical element or prism having a plurality of angularly displaced, adjacent faces in contact with the medium.

In the present probe, separate ATR analyses may be performed simultaneously by having the optical element cut at appropriate angles, for instance using an optical element with multiple facets along two or more planes. A prism with two, sixty degree angles along one plane and cuts at a different angles orthogonal to the plane of the sixty degree cuts are an example. Benefits of such dual faceted optical elements could include the ability to perform ATR and RI measurements. RI may be determined by the critical angle necessary for ATR and the angle of incidence of the light, for example, as follows. A single fiber may direct light to one surface of an ATR prism so the light totally internally reflects and impinges upon one of a plurality of collecting fibers positioned at a plurality of angles with respect to normal of one side of the optical element. Thus, using critical angle refractometry and the well known Snell's law the RI may be determined by the angle of the illuminated optical fiber at the light-dark transition.

The space exterior to the probe may be air or a fluid medium in which the probe is immersed. In addition to immersion, the probe body may be sealed to the process or the probe may be attached to a dip pipe, for instance, to immerse into a process.

With respect to ATR analysis, the effective path of light in a medium being analyzed is approximately proportional to $N/\cos I$, where N is the number of reflections and I is the angle of incidence. The upper limit of the refractive index (n') of the fluid medium is given by the formula $n'+n \sin I$, where n is the refractive index of the prism material. Since the choice of the prism materials is limited, the angle of incidence and/or the number of reflections can be varied to accommodate samples of various refractive indices and absorptivities within geometrical limits and probe constraints.

The system may be calibrated by immersing the probe in two or more calibrating mediums and measuring in each case the intensity of the transmitted light at a wavelength absorbed by a particular constituent in each medium. The calibrating mediums should correspond to that to be analyzed, but should contain known concentrations of the light absorbing constituent. The apparatus then may be used in a similar manner to measure the intensity of transmitted light following immersion of the probe in a like medium containing a like constituent of unknown concentration. The intensities obtained from the calibrating mediums and the medium under analysis may be compared to obtain the concentration of the absorbing constituent in the latter medium.

Turning now to particle detection, prior to the formation of crystals in the medium, the probe is positioned with respect to the medium such that a beam of light to be introduced from the probe can illuminate a zone of the medium. The probe may be introduced through an opening in the wall of the vessel through which the probe is inserted, or the probe may be immersed in the medium so as to illuminate any desired part thereof. Prior to the commencement of crystallization, relatively little or none of the light introduced into the medium is reflected or backscattered toward the probe and onto the optical fiber. Upon the onset of nucleation, however, crystalline particles appear in the illuminated zone of the medium and scatter the incident light in all directions.

Light scattered by an interface between the medium and crystalline particles or another entity having a refractive index differing from the medium in the illuminated zone of the vessel will impinge upon an optical fiber as a signal which will be transmitted by the fiber to a detector means. In general, at low concentration, the intensity of the signal is dependent on the surface area and location of a particle in the illumination zone, and the number of such pulses is directly proportional to the number of crystals traversing the illuminated zone. Interpretation of data obtained from backscatter analysis may be done as described, for example, in U.S. Pat. No. 5,365,326 to Chrisman et al. which is herein incorporated by reference.

EXAMPLES

A probe as depicted in the figures has an ATR channel (FIG. 2) and a particle detection channel (FIG. 3). With respect to the ATR channel, a high performance thirty watt deuterium lamp is used as a light source. The detector is a combination of a diode array CCD Model LS-2000C from Alton Instruments Corp. (Irvine, Calif.) and a miniature spectrograph Model Monospec 18 from Scientific Measurement Systems, Inc. (Grand Junction, Colo.); these two units are physically coupled and accept a fiber optic input with appropriate mounts and optics.

With respect to the particle detection channel, the light source is a high power light emitting diode. The detector is a silicon photodiode.

The detector/light source combination is limited by the light which can be transmitted by the optical fiber. Fused silica core/cladding fiber of 600 micron diameter is used for the UV-ATR channel. Large core (600 micron) single strand optical fiber is used to maximize light collection and transmission efficiency while surviving the process environment. For the particle detection channel, HCS (hard clad silica) fiber of 400 micron diameter is used to transmit 850 nanometer near IR light from the light emitting diode (LED) and has a higher numerical aperture to increase collection efficiency.

Other light sources, such as a laser diode, a continuous wave gas laser, or an incandescent lamp may be used. Similarly, a different compatible photodiode, a photomultiplier tube, or other sensitive light detection device may be used as a detector.

The probe uses a ½" diameter sapphire prism and a ⅝" tubular body, and could be scaled up if necessary. Sapphire lenses which collimate the UV light currently define the minimum probe diameter. Substitute lenses preferably have small diameter, short focal length, and UV transmitting ability. Added angled lenses are less critical because the fiber can be smaller and photons of near IR wavelengths may be transmitted through use of a LED or laser diode.

The materials of construction are chosen to best fit the function of the part, for example, a sapphire optical element to transmit specific wavelengths. The probe body should withstand the corrosion, abrasion, and mechanical loading of the sampled system. For example, a probe used in a crystallizer may need to withstand harsher conditions than a probe used in another application. The internal inserts should be protected from the process. The gasket seals should be resilient to support the prism, yet seal and resist the entry of mother liquor or other fluid medium. A KALREZ™ gasket rated at about −50 to about 316 degrees Celsius is used. The pressure rating of the probe depends on the strength of the spring. Preferably, pins are used to prevent rotation of the prism with respect to the main insert so that light travels reproducibly through the optical element. High temperature epoxy systems such as EPOTEK 354 are used to retain the lenses and fibers in their respective holders. To enhance ATR capabilities, mechanical locks prevent the adjustable parts from moving once alignment is achieved.

While certain representative embodiments and details have been shown for the purpose of illustrating the invention, it will be apparent to those skilled in the art that various changes and modifications can be made therein without departing from the spirit and scope of the invention.

What is claimed is:

1. A probe for spectrometric analysis comprising a means for transmitting light through the probe such that the light interacts with a fluid medium, wherein the improvement comprises: an essentially monolithic optical element suitable for contact with the fluid medium, said optical element being capable of directing the transmitted light so that the transmitted light interacts with the fluid medium to perform at least two simultaneous distinct spectrometric analyses.

2. The probe of claim 1 wherein the spectrometric analyses are selected from the group consisting of attenuated total reflectance, refractive index determination, light scatter analysis, and image analysis.

3. The probe of claim 1 wherein the optical element is capable of directing the light to perform attenuated total reflectance and backscatter analysis.

4. The probe of claim 1 wherein the optical element is capable of directing the light to perform attenuated total reflectance and image analysis.

5. The probe of claim 1 wherein the optical element is capable of directing the light to perform refractive index determination and attenuated total reflectance.

6. The probe of claim 1 wherein the optical element is shaped as a truncated chisel.

7. The probe of claim 1 further comprising a means for focusing light, said means for focusing light being positioned between the optical element and the means for transmitting light.

8. A probe for performing at least two distinct spectrometric analysis on a fluid medium, the probe comprising:

(a) a body having a cavity therein;

(b) an optical element capable of directing light to perform at least two distinct spectrometric analyses on the fluid medium, the cavity being in spectrometric communication with the space exterior to the probe through the optical element;

(c) means for transmitting light to the optical element; and (d) receiving means for receiving the light after the light interacts with the fluid medium.

9. The probe of claim 8 wherein the spectrometric analyses are selected from the group consisting of attenuated total reflectance, refractive index determination, light scatter analysis, and image analysis.

10. The probe of claim 8 wherein the optical element is capable of directing the light to perform attenuated total reflectance and backscatter analysis.

11. The probe of claim 8 wherein the optical element is a single prism.

12. The probe of claim 8 further comprising:

(e) a first light source, the first light source being optically coupled with the means for transmitting light to the optical element; and (f) a second light source, the second light source being optically coupled with the means for transmitting light to the optical element.

13. The probe of claim 8 wherein the means for transmitting light to the optical element comprises:

an input absorbance optical fiber having an end, said input absorbance optical fiber being positioned within the cavity so that the end of the input absorbance optical fiber is optically coupled with the internal surface of the optical element such that light emerging from the one end of the input absorbance optical fiber enters the optical element through the internal surface of the optical element and then is internally reflected in the optical element and then exits the internal surface of the optical element; and an input reflectance optical fiber having an end, said input reflectance optical fiber positioned within the cavity so that the end of the input reflectance optical fiber is optically coupled with the internal surface of the optical element such that light emerging from the end of the input reflectance optical fiber enters the optical element through the internal surface of the optical element and then exits the optical element through the external surface of the optical element to produce an illuminated zone so that if a second phase is in the illuminated zone the light reflected from the second phase can then enter the external surface of the optical element and then exit the internal surface of the optical element;

and the receiving means comprises an output absorbance optical fiber having an end, said output absorbance optical fiber being positioned within the cavity so that the end of the output absorbance optical fiber is optically coupled with the input absorbance optical fiber through the optical element; and an output reflectance optical fiber having an end, said output reflectance optical fiber being positioned within the cavity so that the end of the output reflectance optical fiber is optically coupled with the input reflectance optical fiber through the optical element and the second phase.

14. The probe of claim 13, further comprising a means for focusing light, said means for focusing light being positioned between said optical element and the end of each said absorbance optical fiber.

15. A method of analysis which comprises performing at least two distinct spectrometric analyses on a fluid medium by passing light through a single optical element, wherein the spectrometric analyses are selected from the group consisting of attenuated total reflectance, refractive index determination, light scatter analysis, and image analysis.

16. The method of claim 15 wherein the spectrometric analyses comprise attenuated total reflectance and backscatter analysis.

17. The method of claim 15 wherein the spectrometric analyses comprise attenuated total reflectance and refractive index determination.

18. The method of claim 15 wherein the spectrometric analyses comprise attenuated total reflectance and image analysis.

* * * * *